US008388689B2

(12) United States Patent
Orbay et al.

(10) Patent No.: US 8,388,689 B2
(45) Date of Patent: Mar. 5, 2013

(54) ALIGNABLE PROSTHESES SYSTEM AND METHOD

(75) Inventors: Jorge L. Orbay, Miami, FL (US); Thomas H. Norman, Miami, FL (US); William Garcia de Quevedo, Miami, FL (US)

(73) Assignee: Skeletal Dynamics, LLC, Miami, FL (US)

( * ) Notice: Subject to any disclaimer, the term of this patent is extended or adjusted under 35 U.S.C. 154(b) by 89 days.

(21) Appl. No.: 12/852,035

(22) Filed: Aug. 6, 2010

(65) Prior Publication Data

US 2011/0035016 A1  Feb. 10, 2011

Related U.S. Application Data

(60) Provisional application No. 61/231,859, filed on Aug. 6, 2009, provisional application No. 61/238,463, filed on Aug. 31, 2009.

(51) Int. Cl.
*A61F 2/38* (2006.01)
*A61F 2/02* (2006.01)
(52) U.S. Cl. ............... 623/20.11; 623/19.14; 623/23.42; 623/23.44; 623/23.47; 606/99
(58) Field of Classification Search ............... 623/19.14, 623/20.11–20.13, 23.42, 23.44, 23.47; 606/99, 606/267
See application file for complete search history.

(56) References Cited

U.S. PATENT DOCUMENTS

| 5,741,335 | A | 4/1998 | Gerber et al. |
| 5,779,709 | A * | 7/1998 | Harris et al. ............ 606/87 |
| 5,879,395 | A | 3/1999 | Tornier et al. |
| 6,117,175 | A | 9/2000 | Bosredon |
| 6,206,925 | B1 * | 3/2001 | Tornier ............ 623/19.12 |
| 6,228,120 | B1 | 5/2001 | Leonard et al. |
| 6,270,529 | B1 | 8/2001 | Terrill-Grisoni et al. |
| 6,334,874 | B1 * | 1/2002 | Tornier et al. ........... 623/19.14 |
| 6,656,225 | B2 | 12/2003 | Martin |
| 7,160,329 | B2 | 1/2007 | Cooney, III et al. |
| 2004/0147936 | A1 * | 7/2004 | Rosenberg et al. ........ 606/99 |
| 2005/0085921 | A1 | 4/2005 | Gupta et al. |
| 2005/0182406 | A1 * | 8/2005 | Orbay et al. ............ 606/69 |
| 2006/0217716 | A1 * | 9/2006 | Baker et al. ............ 606/61 |
| 2006/0217737 | A1 * | 9/2006 | Iversen ............ 606/102 |
| 2008/0114461 | A1 * | 5/2008 | Collazo ............ 623/19.14 |
| 2009/0240336 | A1 | 9/2009 | Vander Meulen et al. |

FOREIGN PATENT DOCUMENTS

WO  2007109752 A2  9/2007

* cited by examiner

*Primary Examiner* — David Isabella
*Assistant Examiner* — Randy Shay
(74) *Attorney, Agent, or Firm* — Laurence A. Greenberg; Werner H. Stemer; Ralph E. Locher

(57) ABSTRACT

A prosthesis is provided for replacing a portion of a bone making up a joint. The prosthesis is adapted, intraoperatively, to optimize the anatomical alignment of the prosthesis in the joint. In particular, a jig is used to identify the axis of rotation of the joint intraoperatively and to align a portion of the prosthesis with the identified axis. The angle of the head of the prosthesis is adjusted to optimize contact with the appropriate corresponding portions of the joint, at which point the position of the head is fixed to prevent further rotation of the head relative to the remainder of the prosthesis.

21 Claims, 19 Drawing Sheets

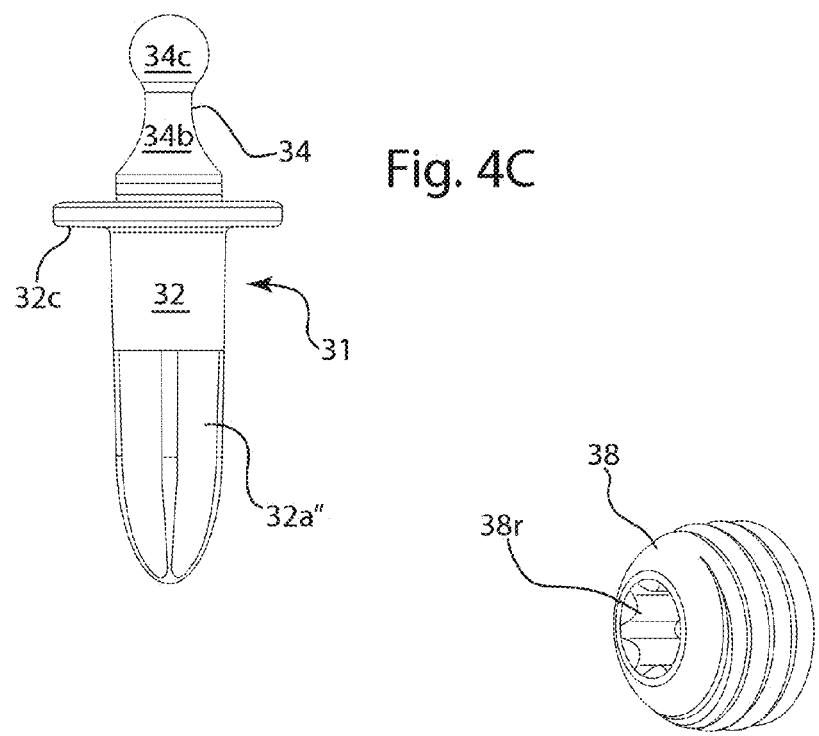
Fig. 4C
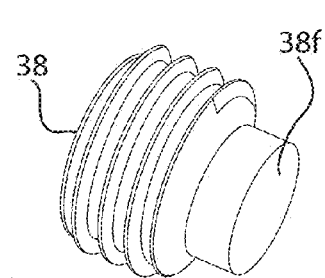
Fig. 5B
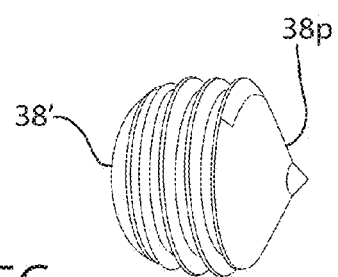
Fig. 5A
Fig. 5C

ALIGNABLE PROSTHESES SYSTEM AND METHOD

CROSS-REFERENCE TO RELATED APPLICATIONS

The present application claims priority to: Provisional Patent Application No. 61/238,463, filed on Aug. 31, 2009 and Provisional Patent Application No. 61/231,859, filed on Aug. 6, 2009, both entitled "Alignable Prostheses Device, System and Method", those applications being incorporated herein, by reference, in their entireties.

BACKGROUND OF THE INVENTION

1. Field of Invention

The present invention relates to a prostheses device, system and method for replacing a portion of bone forming a part of a joint, and more particularly to a prosthesis device that is positionable, in situ, in the correct anatomical alignment with the joint and to a system and method for aligning the prosthesis, intraoperatively.

2. Description of the Related Art

Prostheses systems for replacing part of a joint are known in the art. For example, in connection with the elbow joint, modular prostheses systems for replacing the head of the radius exist that provide for replicating the different diameters of a resected radial head, as well as, for allowing adjustability of the overall length of the prostheses. These known devices permit a surgeon to install a radial head prosthesis that generally approximates the original geometrical relationship between the radial head, the capitellum of the humerus and the radial notch of the ulna.

For example, U.S. Pat. No. 6,270,529 (the "'529 patent") to Terrill-Grisoni discloses a modular implant and system for replacing the radial head. The system of the '529 patent includes modular radial head implants, sizers for trial reduction of the joint, and instrumentation for preparing the radial head, trialing the sizers, and assembling the implants. Similarly, U.S. Pat. No. 6,656,225 (the "'225 patent") to Martin discloses a modular radial head prostheses and system including a stem component having an anchoring portion and a mounting portion, and a head component having an open channel wherein the open channel is configured to connect to the mounting portion along an assembly axis that is transverse to a longitudinal axis of the stem component. Although such modular, adjustable prostheses provide for some degrees of adjustability of the position of the radial head prosthesis to the capitellum of the humerus, the ability to provide even further degrees of adjustability would be advantageous. In particular, since these devices do not explicitly address the angular alignment of the prosthesis to the capitellum in the relevant planes it has been observed that, after implantation, they can "wobble" in the joint in a way similar to the wobble of the wheel of a vehicle that is not correctly aligned to its axle.

In an attempt to address the alignment issue other types of radial head prostheses have been devised wherein the prosthetic radial head is allowed to swivel freely, within a certain range, relative to the medullary canal of the radius bone. For example, U.S. Pat. No. 5,879,395 to Tornier et al., (the "'395 patent"), discloses an elbow prosthesis including a radial element having an anchoring stem provided with a neck which is inclined by an angle of between 0 and 30 degrees relative to the axis of the anchoring stem. In the '395 patent, the neck is integral with a ball on which a cylindrical head articulates. Such devices are known in the art as "bipolar" prostheses. Other bipolar prostheses are disclosed in United States Patent Application Publication No. 2006/0142866 to Baratz and in PCT Application Publication No. WO07/109,752 to Vander Meulen. Additionally, a bipolar prosthesis, in the context of a radial-capitellar implant, is disclosed in U.S. Pat. No. 7,160,329 to Cooney.

While these types of prostheses intend to reduce or eliminate the wobble, it has been noted that, rather than provide the correct alignment of the radial head prosthesis to the capitellum, bipolar prostheses allow for multiple alignments of the head that constantly change as the joint traverses through its natural range of motion and are prone to lock themselves into an extreme alignment, leading to subluxation and/or continued instability of the joint.

What is needed is a device, system and method that overcomes the disadvantages of known prostheses. In particular, there is needed a device, system and method for replacing a portion of a bone making up a joint, wherein the natural axis of rotation of the joint can be identified intraoperatively, and wherein the prosthesis can be fixed in the identified anatomical alignment of the joint.

SUMMARY OF THE INVENTION

It is accordingly an object of this invention to provide an alignable prostheses device, system and method that overcomes the above-mentioned disadvantages of the heretofore-known devices. More particularly, a prosthesis device and system is provided for replacing a portion of a bone making up a joint. The prosthesis is intraoperatively adjusted and thereafter fixed in position in the proper anatomical alignment of the joint. In one particular embodiment of the invention a jig is used to determine the axis of rotation of the joint and a portion of the prosthesis is adjusted and fixed in alignment with the determined axis.

Although the invention is illustrated and described herein as embodied in an Alignable Prostheses Device, System and Method, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

FIG. 4C is a side elevational view of a further exemplary embodiment of a unitary stem that can be used with a prosthesis device in accordance with the present invention.

FIG. 5A is a perspective view of a set screw that can be used with a prosthesis device in accordance with the present invention viewed from the tool engaging side.

FIG. 5B is a perspective view of one particular embodiment of set screw that can be used with a prosthesis device in accordance with the present invention viewed from the side opposite to the tool engaging side.

FIG. 5C is a perspective view of a further particular embodiment of a set screw that can be used with a prosthesis device in accordance with the present invention viewed from the side opposite to the tool engaging side.

DETAILED DESCRIPTION OF THE INVENTION

The present invention relates to a device, system and method for replacing a portion of bone making up one part of a joint, such that the device replacing the bone portion can be installed with the correct geometry and alignment, that is, as close as possible to the original anatomical geometry and alignment of the native bone portion. For purposes of simplifying the description herein, the invention will be described in connection with the replacement of the radial head portion of an elbow joint. However, it will be understood from the following description that the device, system and method of the invention can be adapted for use with other joints of the body.

Figure 1A:
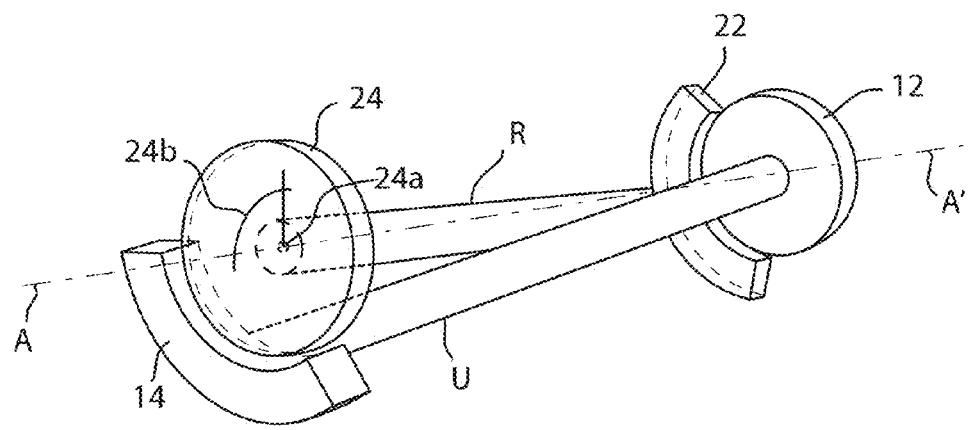
FIGS. 1A and 1B figuratively illustrate the interaction between the radius and ulna bones of a human arm.
Figure 1B:
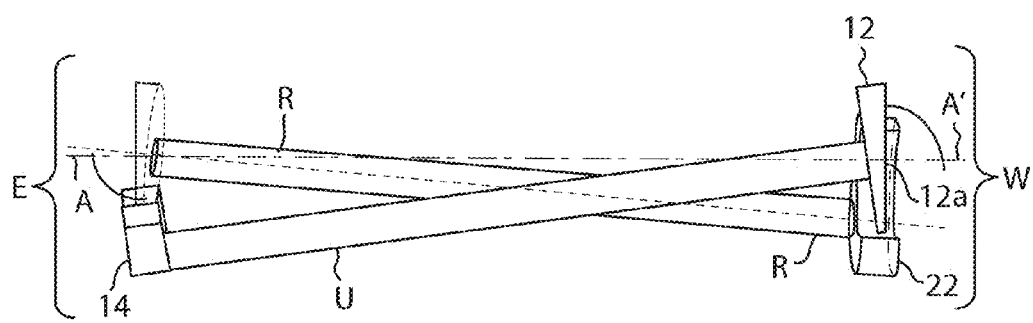

More particularly, referring now to FIGS. 1A and 1B, there is shown a figurative representation of the interaction between the ulna U and radius R bones of a human arm. At the elbow, or proximal joint E, the radial notch 14 of the ulna U and the radial head 24 of the radius R bone interact with each other, and with the capitellum of the humerus (not shown) to permit the movement of the elbow. At the wrist, or distal joint W, the ulnar notch 22 of the radius R articulates through interaction with the head 12 of the ulna U. An axis of rotation of the forearm A-A' can be located, not from the geometry of the radius alone, but rather, from a line passing through the fovea 24a of the radial head 24 and through the fovea 12a of the ulnar head 12. It has also been observed that an imaginary plane tangential to the fovea 24a of the radius forms a right angle 24b with the axis A-A' (i.e. it is perpendicular to A-A').

In accordance with the instant invention, a prosthesis device 30 is provided to replace a portion of a bone that makes up a part of a joint. In the present particular embodiment, the device 30 is a prosthesis device for replacing a damaged radial head.

Figure 2:
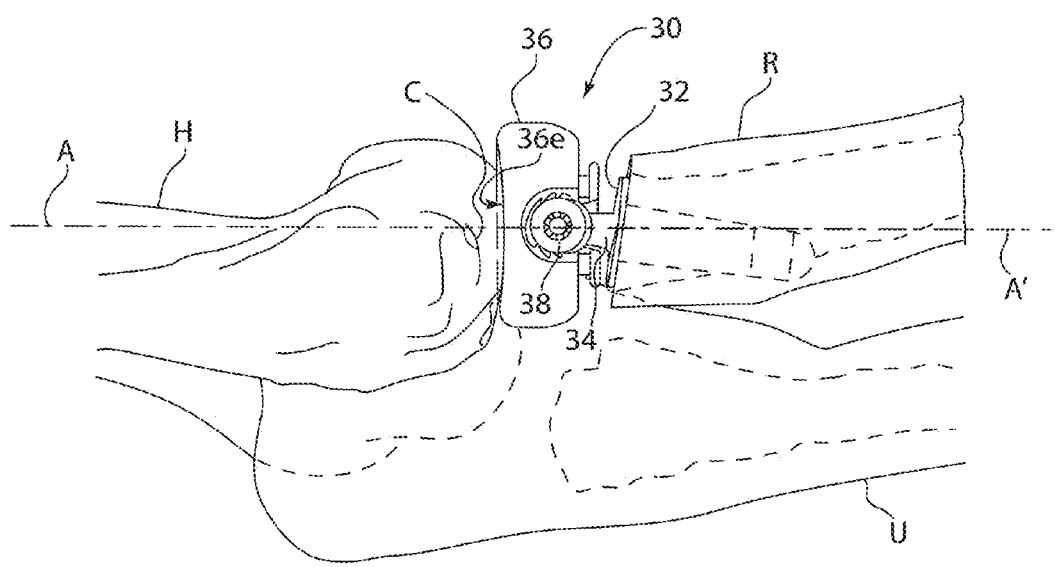
FIG. 2 is a view of a prosthesis device installed in the elbow where the articular surface of the radial head prosthesis is correctly aligned in the relevant planes relative to the capitellum and the radial notch.

Referring now to FIG. 2, there is shown one particular embodiment of a prosthesis device and system installed in an elbow joint, in accordance with the present invention. In particular, when replacing the head of the radius R with a prosthesis device 30, an optimal result can be achieved by fixing the center of concave articular surface 36e of the prosthesis head 36 at the correct anatomical alignment with the capitellum C of the humerus H. As previously observed, the correct anatomical alignment of the prosthesis head is defined by an imaginary plane tangential to the bottom of the concave surface 36e (i.e. the deepest portion, or "dish" corresponding to the fovea of the anatomical radial head) that is perpendicular to the axis A-A' around which the forearm rotates through its range of motion at the elbow. The instant invention relates to a prosthesis device, system and method that intraoperatively allows the surgeon to align, and then fix the head of the prosthesis at the correct anatomical orientation (i.e. perpendicular to axis A-A').

Figure 3A:
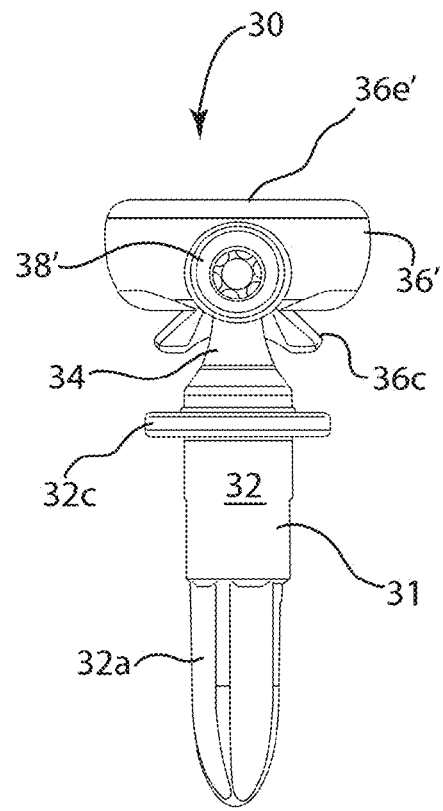
FIG. 3A is a front elevational view of a prosthesis device in accordance with one particular embodiment of the invention.
Figure 3B:
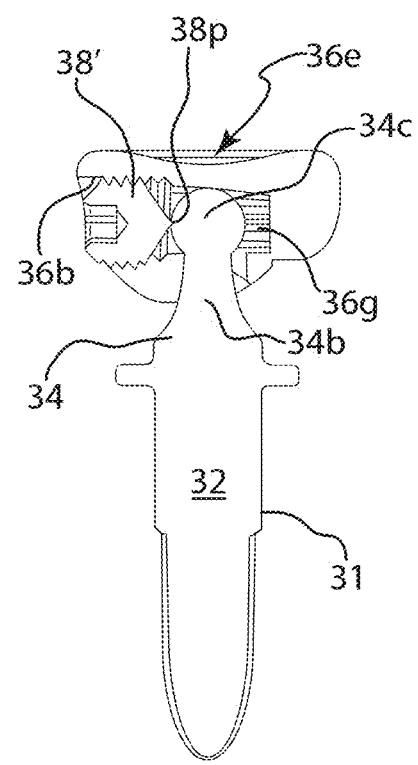
FIG. 3B is a side cross sectional view of the prosthesis device of FIG. 3A.
Figure 3C:
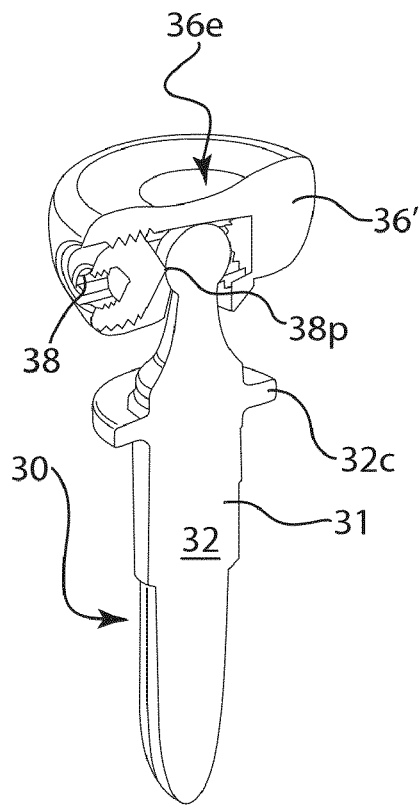
FIG. 3C is a perspective cross-sectional view of the prosthesis device of FIG. 3A
Figure 3D:
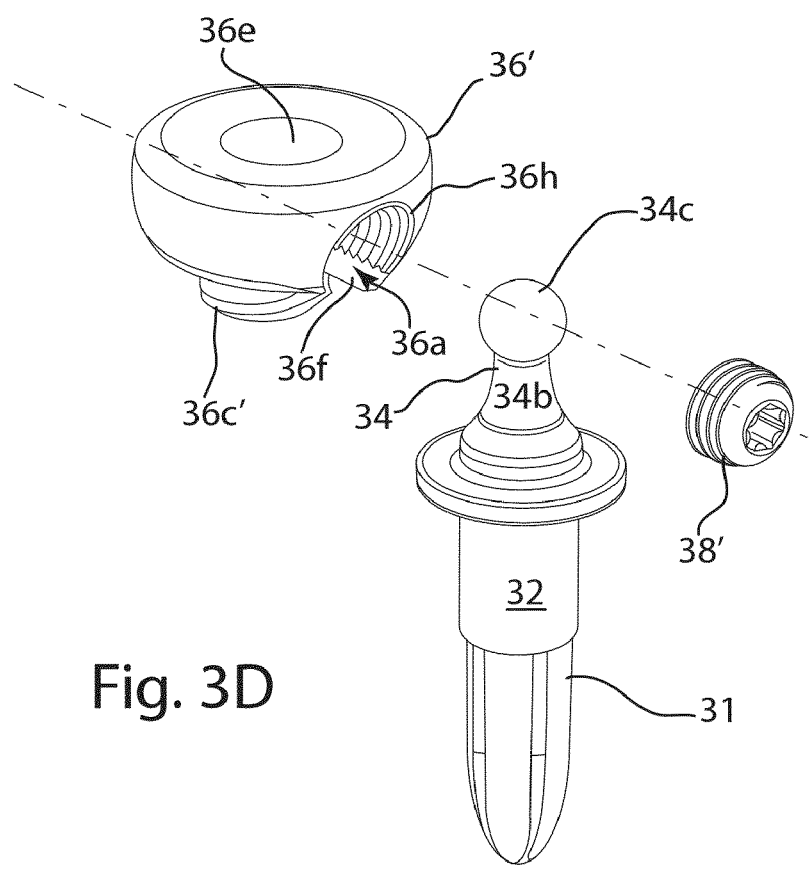
FIG. 3D is an exploded view of the prosthesis device of FIG. 3A.

More particularly, and as can more clearly be seen in FIG. 3D, the prosthesis device 30 is shown to be formed from three major components: a stem 31, a head 36' and a set screw 38', to be further described below.

The stem 31 is designed, in part, for anchoring into the medullary canal of the radius, after removal of the radial head. As seen in FIGS. 3A-3D the stem 31 includes a distal medullary anchor portion 32; a flange 32c, which is sized and located to seat flush with a cut made to the bone during surgery as shown more clearly in FIG. 2, and a proximal neck portion 34 designed to engage into a cavity or chamber in the head 36' of the prosthesis device 30. Further, the neck portion 34 includes a narrowed waist section 34b and, more distally, a ball portion or spherical protuberance 34c which permits free rotation (i.e., swiveling) within the aforementioned chamber or cavity within the head 36', until intentionally restrained by the surgeon into a desired, correctly aligned, permanent position. In one particular example, the "desired, correctly aligned, permanent position" corresponds to a position wherein the imaginary plane tangential to the bottom of the concave surface 36e is fixed at a desired angle relative to an axis running through the length of the stem 31. When fixed at this "desired angle", the imaginary plane is actually perpendicular to (i.e., at a right angle to) the axis of rotation of the joint.

Figure 3E:
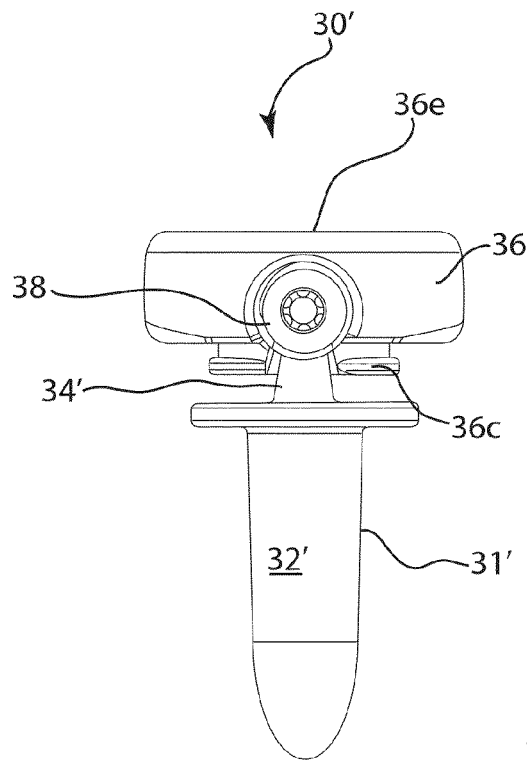
FIG. 3E is a front elevational view of a prosthesis device in accordance with an alternate embodiment of the invention.
Figure 3F:
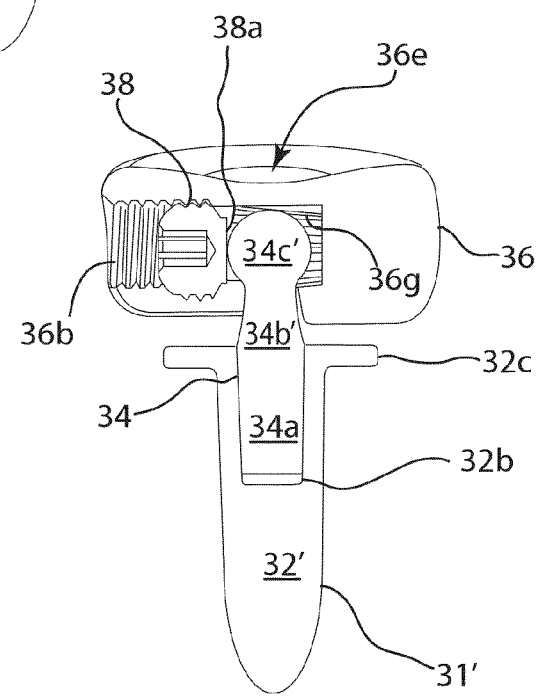
FIG. 3F is a cross sectional view of the prosthesis device of FIG. 3E
Figure 3G:
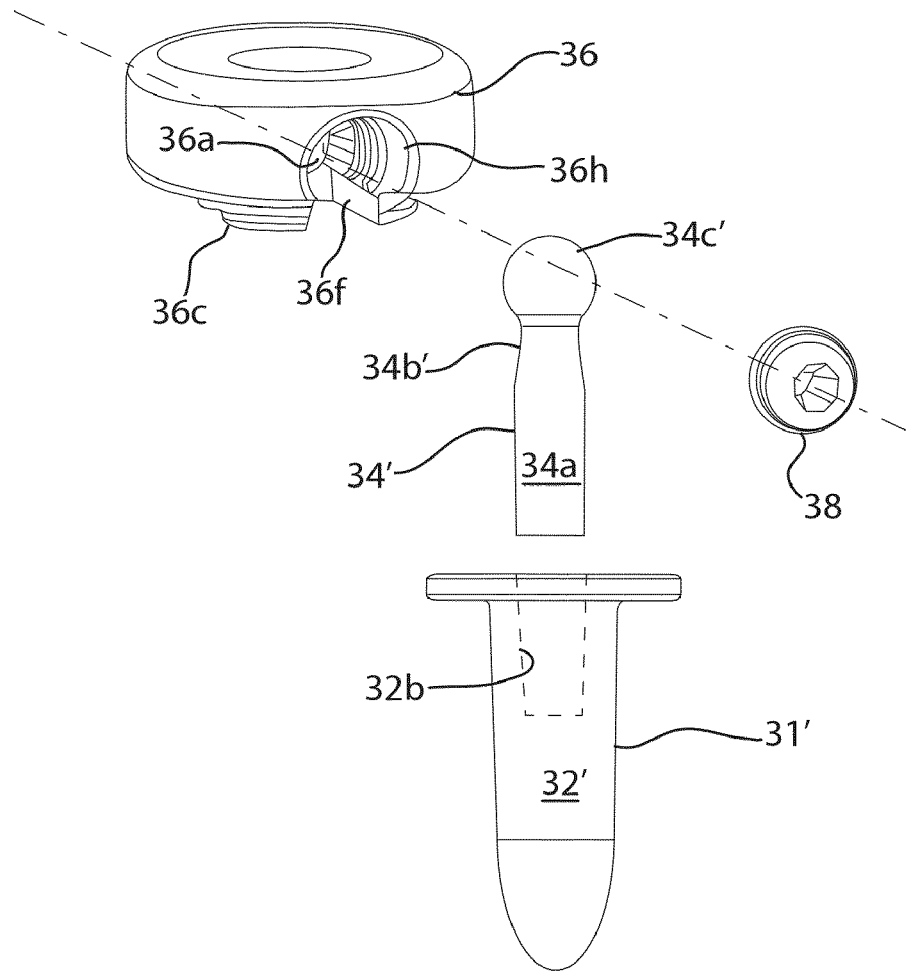
FIG. 3G is an exploded view of the prosthesis device of FIG. 3E

Referring now to FIGS. 3E-3G, therein is shown an alternate embodiment of prostheses device 30', in particular as it refers to a different configuration of stem 31'. In this particular embodiment the neck portion 34' of stem 31' is configured as a separate piece, i.e. not integral with, the stem 31', but intended to become integral when purposely linked (i.e., "mated") with the distal medullary anchor portion 32'. As can better be appreciated in FIG. 3B of the presently described embodiment, the distal medullary anchor portion 32' further includes a central bore 32b extending into the body of the medullary anchor portion 32'. The central bore 32b is configured to receive, and permanently engage, the congruently configured pin end 34a of a neck 34', as will be described more particularly herebelow. Medullary anchor portions 32' are sized to adapt to different anatomical medullary canal diameters while necks 34' vary in length to adapt to different gaps left by the removal of a damaged native radial head. The advantageous purpose of having the neck portion 34' as a separate but permanently joinable adjunct to medullary anchor portion 32' is to increase the number of possible combinations achievable to adapt to different surgical situations. For example, providing medullary anchor portions 32' in five different diameters and neck portions 34' in five different lengths permits attaining 25 different combinations with only 10 discrete pieces.

In one particularly preferred embodiment of the prosthesis device 30', the central bore 32b of the distal medullary anchor portion 32' has a tapered design (i.e. a Morse taper) that corresponds to a taper formed on the pin portion 34a of the neck 34'. This taper will assure the permanent attachment of the pin portion 34a of the neck 34' to the central bore 32b of the distal medullary anchor portion 32', once mated. In the instant embodiment of the invention, the anchor portion 32' and neck 34' are mated prior to the insertion of the stem 31' into the medullary canal of the radius. In one particular embodiment, a block is provided having a central bore dimensioned to receive the anchor portion of largest diameter. This block can hold the anchor portion 32' while tapered portion 34a of the neck 34' is engaged with the central bore 32b of the anchor portion 32', for example, by a tap from a hammer. It should be noted that once this is accomplished the construct becomes essentially unitary and functionally identical to unitary stem 31 of FIGS. 3A-3D.

Figure 4A:
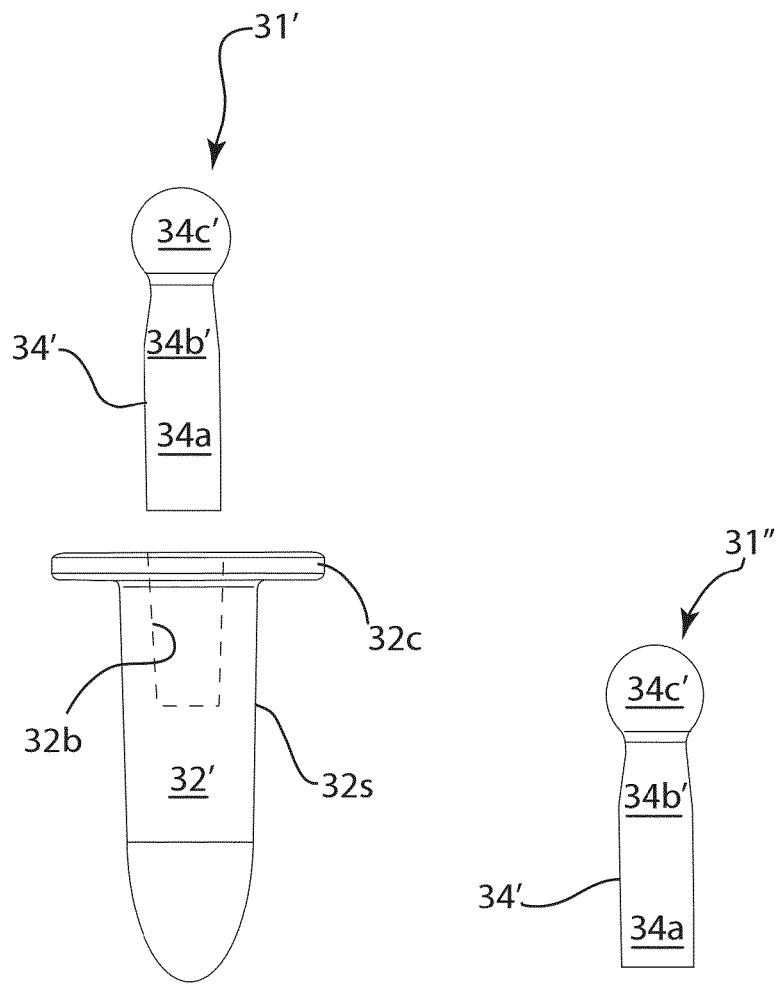
FIG. 4A is an exploded front elevational view of an alternate exemplary embodiment of a combined distal medullary anchor and a neck that can be used with a prosthesis device in accordance with the present invention.
Figure 4B:
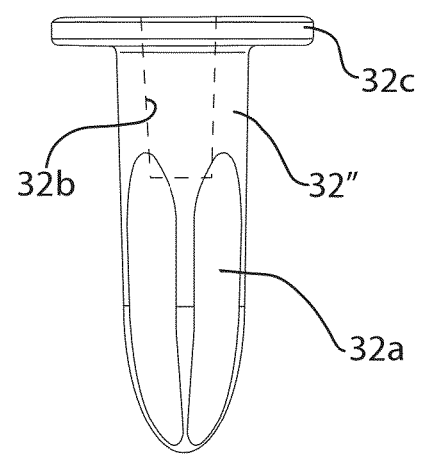
FIG. 4B is an exploded front elevational view of a further embodiment of a combined distal medullary anchor and neck useful with one particular embodiment of the present invention.

Referring now to FIGS. 4A-4C, there are shown different alternative embodiments of stem 31, all made of a bio-compatible metal such as titanium. The stems 31', 31" of FIGS. 4A and 4B are representative of the embodiment where the neck 34' and the distal medullary anchor 32', 32" are separate parts intended to be joined permanently after the proper size of each part has been determined and selected by the surgeon. Conversely, FIG. 4C is a unitary embodiment of stem 31. Furthermore, in one particular preferred embodiment of the distal medullary anchor 32s of FIG. 4A is bullet shaped and is roughened, for example, by the application of titanium plasma spray, TCP or other coating as desired. In FIG. 4B, the distal medullary anchor 32" includes the flutes 32a, to assist in the insertion of the anchor 32" into the medullary canal and, once inserted, to resist rotation of the anchor 32" within the medullary canal. FIG. 4C shows a unitary stem 31 where the distal medullary anchor 32 is fluted in its distal portion with flutes 32a. The distal medullary anchor 32 can additionally be treated with titanium plasma spray in its most proximal portion, up to the underside of the flange 32c, if desired. Other sizes and shapes of stem can be made and used in place of those shown. Note that the provision of these particular examples of stems is not meant to limit the invention only thereto, as further sizes body shapes, coatings and flange shapes can be selected, as desired.

Referring now to FIGS. 5A-5C, there is shown an enlarged view of a set screw 38, the purpose of which is to lock the head 36 to the neck 34, at a desired orientation (i.e., a "desired angle"). FIG. 5A shows a set screw 38 having a tool engaging recess 34r, which, in this embodiment, is hexalobular. The recess 38r can also be slotted, Allen, Phillips and/or another desired configuration. FIG. 5B shows a set screw 38 with a flat distal end 38f (i.e., the end that abuts the neck portion). Conversely FIG. 5C shows a set screw 38' with a pointed distal end 38p. Set screws 38, 38', as well as head 36, are preferably made of a bio-compatible metal harder than titanium, such as cobalt-chromium, to insure secure fixation of the titanium neck ball 34c to the cobalt chromium head 36 with the set screw 38, 38'.

In one particular embodiment of the invention, the final prosthesis device 30 used during a surgical procedure can be assembled from a variety of components that are provided to the surgeon as part of a kit. For example, such a kit could contain a plurality of prosthesis stems 31 and/or 31', and/or distal medullary anchors 32 and/or 32', i.e., having separate necks 34 and/or unitary anchors and necks, and heads 36 and/or 36' of varying dimensions so as to provide the surgeon with the best possible choice for adapting the prosthesis device to best approximate the radial head being replaced. In one particular embodiment a kit having distal medullary anchors 32 of five different diameters and/or lengths, necks 34 of five different lengths and heads 36 of five different diameters are provided to be used interchangeably, thereby providing 125 possible combinations from a set of 15 discrete parts. In another embodiment, 25 unitary stems 31 with diverse diameters and neck lengths are provided, which combined with the 5 heads 36 of varying diameters also are capable of delivering 125 possible combinations from a set of 30 discrete pieces. Note that this is not meant to be limiting, as fewer or more choices can be provided without deviating from the scope of the instant invention. Note that, the system of the present invention can be provided as such a kit, as described herein, or as individual devices and/or components, i.e., not as part of a kit, as desired.

In all cases of the embodiment for the stem 31, 31' (unitary or with separate neck portion) the ball 34c of the neck 34 engages a cavity of the prosthesis head 36 (or head 36' of FIGS. 3A-3C and 6F-6G), permitting the conical swiveling (i.e., rotation) of the head 36 to the proper angle α of the correct anatomical alignment of the head 36 and the capitellum of the humerus. Once oriented in the correct anatomical alignment in all the relevant planes, the conical angle "α" of the head relative to the neck ("α" being that unique conical angle which makes an imaginary plane tangential to the bottom of dish 36e of the radial head perpendicular to forearm axis of rotation A-A',—see FIG. 20) is fixed by inserting and tightening the set screw 38 until it presses against the ball 34c, locking the ball 34c and head 36 into the desired orientation (i.e., desired angle). As can be seen more particularly from FIGS. 3A-3G and FIG. 20, the neck 34 of the prosthesis 30 is additionally used to maintain a distance between the upper surface of the flange 32c of the stem and the lower surface of a lug 36c of the head 36. The waist portion 34b of the neck 34, additionally facilitates the swiveling of the head 36 on the ball 34c. The permissible range of motion of the head 36 relative to the neck 34 is determined by the dimensions of the waist portion 32c combined with dimensions of the shoulders of the cavity 36a.

As shown in FIGS. 6A-6G the prosthesis head 36, 36' has a concave proximal articular surface or dish 36e, that engages the capitellum of the humerus. As mentioned above, in one particular embodiment, the head 36 and the set screw 38 are chosen to be made of a bio-compatible metal harder than titanium, such as cobalt-chromium. The underside of the head 36 includes a cavity 36a, which opens out from an opening 36h through the sidewall of the head 36. A channel 36f extends along the bottom of the cavity 36a from the opening through the sidewall to a location past the center of the head 36. The channel 36f engages the waist portion 34b of the neck 34 and entraps the ball 34c in the cavity 36a, once the ball 34c passes through the opening 36h in the sidewall of the head 36. It should be noted that the opening 36h in the sidewall of the head 36 permits the head 36 to be mounted onto the ball 34c from the side, intraoperatively.

Additionally, a portion of the cavity 36a includes a thread 36b for engaging a set screw 38, when the set screw 38 is inserted through the sidewall opening 36a and advanced into the cavity 36a. Thread 36b is preferably of the anti back-out self-locking type such as Spiralock™ or similar. The set screw 38 (see FIGS. 5A-5C) has a flattened distal portion 38a and a thread 38b. Alternately, the set screw 38' of FIG. 5C, having a pointed distal portion 38p, can be used. As described and shown herein, the male thread 38b threadably engages the female thread 36b to guide the set screw into and out of the cavity 36a. The set screw 38, 38' is advanced using a tool, such as an Allen or hexalobular wrench or other type of driver engaged with the tool engaging portion 38r of the set screw 38, 38'. As shown more particularly in FIG. 6E, the cavity 36a can include splines 36g, which will bite into the ball 34c when the set screw 38 is tightened against the ball 34c, to prevent any further swiveling (i.e., rotation) of the head 36 on the ball 34c after the desired positioning of the head has been achieved and ball 34c has been fixed against a rear surface of the cavity 36a by the set screw 38, 38'.

Further and referring again to FIGS. 6A-6E, in accordance with one particular embodiment of the invention, the underside of the head 36 is provided with a lug 36c, which projects away, i.e. distally, from the bottom surface of the head 36. Note that, the channel 36f additionally passes through a portion of the lug 36c. In the present embodiment, the lug 36c is additionally provided with depressions 36d that allow the lug 36c to be gripped by a tool in only one particular orientation and rotated, as will be described more fully herebelow.

Figure 6A:
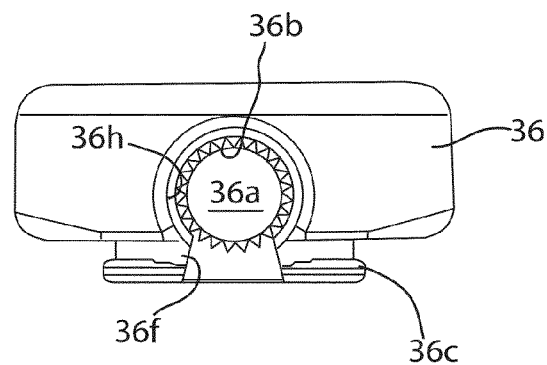
FIG. 6A is a front elevational view of a head portion of a prosthesis device in accordance with one particular embodiment of the present invention.
Figure 6B:
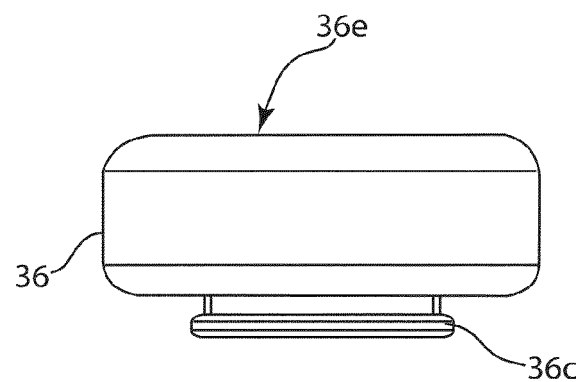
FIG. 6B is a rear elevational view of a head portion of FIG. 6A.
Figure 6C:
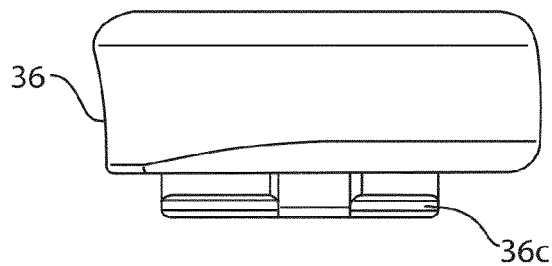
FIG. 6C is a side elevational view of a head portion of FIG. 6A.
Figure 6D:
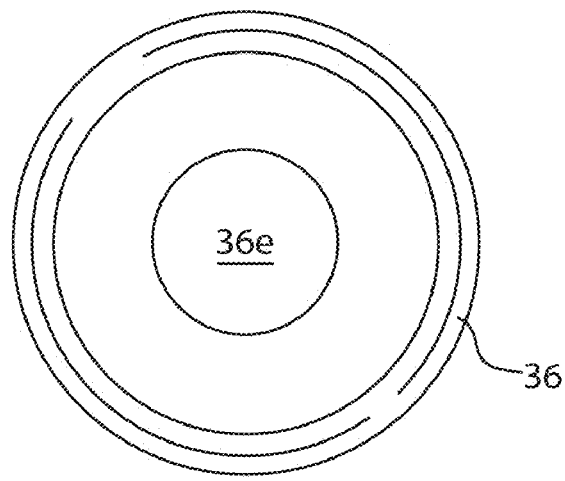
FIG. 6D is a top plan view of a head portion of FIG. 6A.
Figure 6E:
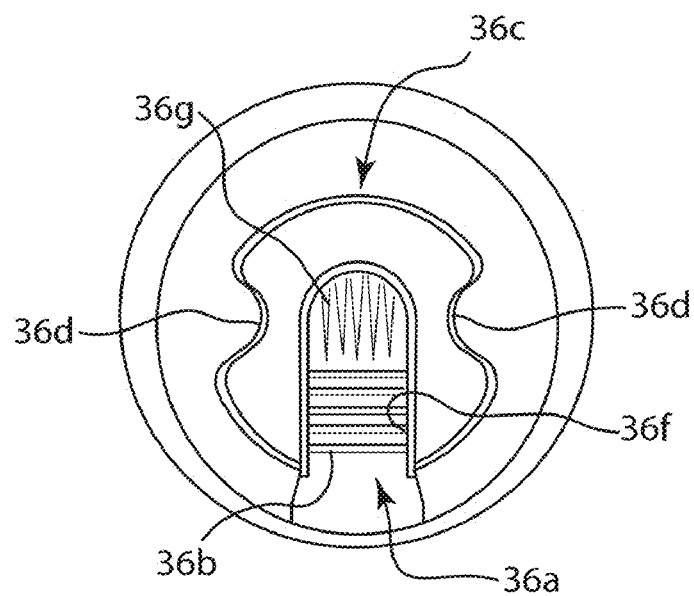
FIG. 6E is a bottom plan view of a head portion of FIG. 6A.
Figure 6F:
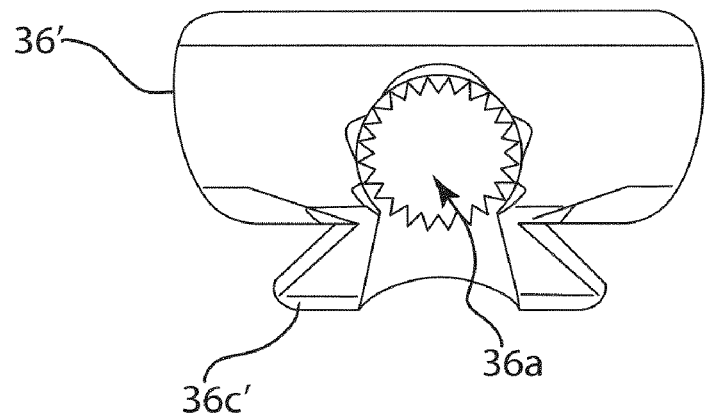
FIG. 6F is a front elevational view of a head portion of a prosthesis device in accordance with another embodiment of the present invention.
Figure 6G:
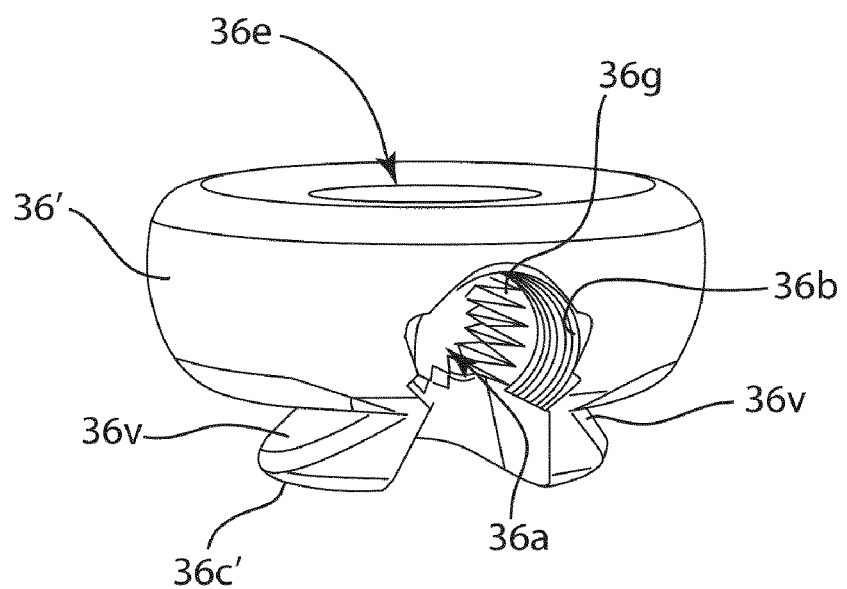
FIG. 6G is a perspective view of the head portion of a prosthesis device of FIG. 6F.

A further embodiment of a prosthesis head 36' is shown in FIGS. 6F-6G. The prosthesis head 36' is similar to the prosthesis head 36, with like item numbers referring to similar elements. However, the lug 36c' of the prosthesis head 36' includes a "dovetail" or "V" shaped groove 36v in substitution of the depressions 36d of the prosthesis head 36 of FIG. 6D. Note that other forms of mating lug portion can be provided on a prosthesis head and still be in keeping with the spirit of the present invention.

Figure 7:
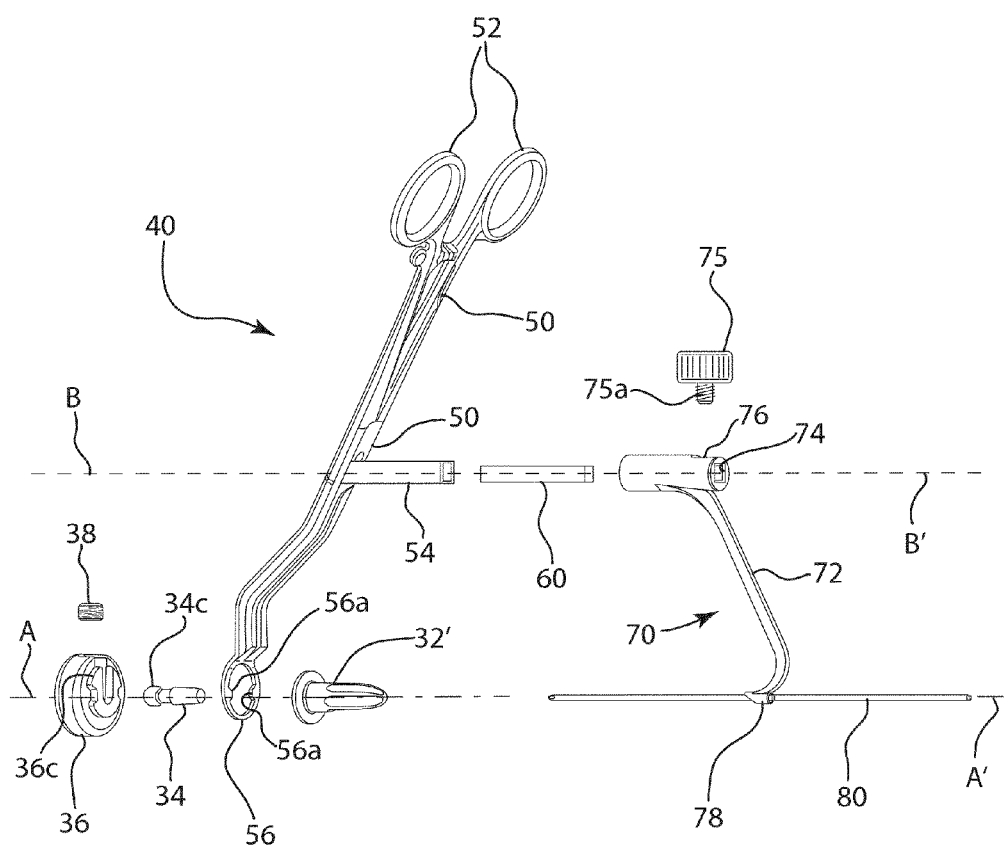
FIG. 7 is a partial exploded view of one embodiment of a prosthesis system for performing the method of the present invention.

Referring now to FIG. 7, there is shown a system including the prosthesis device 30 made up of a prosthesis head 36, set screw 38, neck 34 and distal medullary anchor portion 32, as well as a jig 40 for aligning the head 36 at the correct anatomical alignment relative to the forearm axis or rotation A-A'.

The jig 40 includes a clamp 50, a spacing bar 60, a tail piece 70 and knob 75 having a set screw portion 75a extending through a threaded hole 76 into a bore 74 of the tail piece 70. A K-wire 80, or other type of alignment pin or pointer, is provided at the lower portion of the extension 72 of tail piece 70, through the brace 78. The spacing bar 60 is used to space the tail piece 70 from the clamp 50 and is sized to extend beyond the length of the forearm. As shown in FIG. 7, the spacing bar 60 is fixed at the proximal end to a bracket engaged with the clamp 50, and, at the distal end, with a bore extending through a portion of the tail piece 70. As such, the length of the jig 40 can be adjusted by loosening the knob 75 and moving the tail piece 70 forward or back along the length of the spacing bar 60. The jig 40 is locked in at its desired length by tightening the knob 75 to press the set screw portion 75a of the knob 75 against the spacing bar 60 in the bore 74 of the tail piece 70.

The clamp 50 includes a scissor handle 52 at a first end and a clamping portion 56 at a second, opposite end. The clamping portion 56 is designed to securely engage a portion of the prosthesis head 36. In the present particular embodiment, the clamping portion 56 is designed to engage and grip the lug 36c of the head 36. In the instant embodiment, the clamping portion 56 further includes protuberances 56a (see, for example, FIG. 6E) that mate with the depressions 36d to provide the surgeon with a precise, known alignment of the clamp 50 to the head 36.

Figure 8:
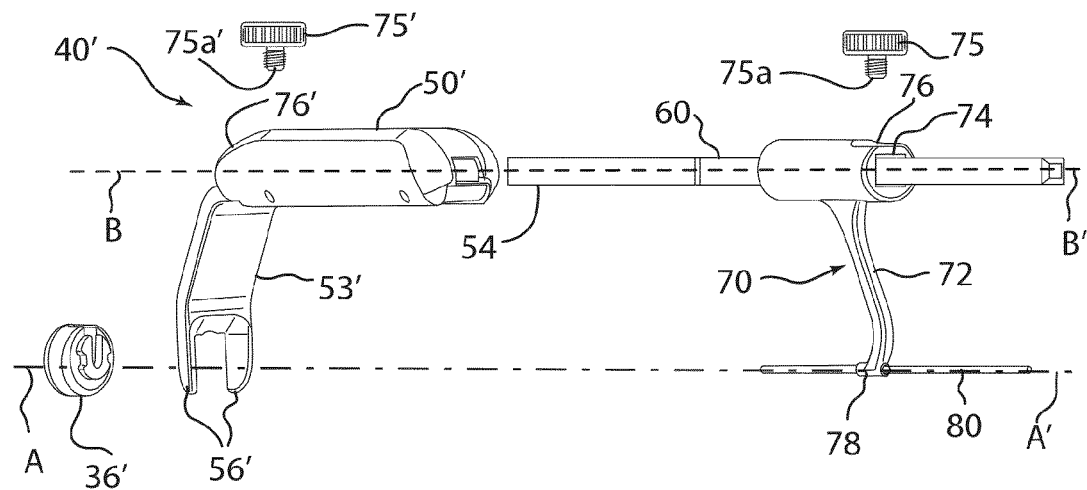
FIG. 8 is a partial exploded view of another embodiment of a prosthesis system for performing the method of the present invention.

Note that the protuberances 56a may be substituted or other forms of keying structures can be provided. For example, as shown in FIG. 8 the scissor clamp 50 of jig 40 is substituted by a handle 50' with a blade extension 53' having at its distal end two parallel prongs 56' configured to engage with complementarily shaped dovetail sidewalls 36v of head portion 36' of FIGS. 6F-6G. As can be seen, the handle 50' of FIG. 8 includes a further knob 75' and screw portion 75a', for mating with a threaded hole 76' (not visible) in the handle 50', for locking the position of the handle 50' at a relative position along the spacing bar 60, which passes through the bore 54' of the handle 50'.

Referring now to tailpiece 70, it is the function of this tailpiece to facilitate the location of a first point on the forearm axis of rotation A-A', particularly a point in proximity to the distal A' side of the axis. As previously explained it is known that such a point exists in the fovea 12a at the wrist joint of the ulna. To locate one such point a K-wire can be inserted into the ulnar fovea 12a, as further described below, and then, the brace 78 of tailpiece extension 72 is inserted over the K-wire and slid it proximally until it abuts with the entry point of the K-wire into the ulnar fovea 12a. This assures that the point of abutment is one point on the axis of rotation A-A'. It should be observed that the construction of the jig 40 is such that the dimension of tailpiece extension 72 is identical to the distance between the centerline of spacing bar 60 and the center of clamping portion 56 of scissor clamp 50. In other words, the axis B-B' of spacing bar 60 is always equidistant (i.e. parallel) to axis A-A'.

The construction of clamp 50, as well as alternative handle 50', is such that, when engaging a prosthesis head 36, 36', the axis of the engaged prosthesis head 36, 36' is made co-linear with axis A-A' passing through the center of clamping portion 56 or parallel prongs 56'. This assures perpendicularity between an imaginary plane tangent to the deepest portion of dish 36e of head 36 and axis of rotation A-A', as desired.

Figure 9:
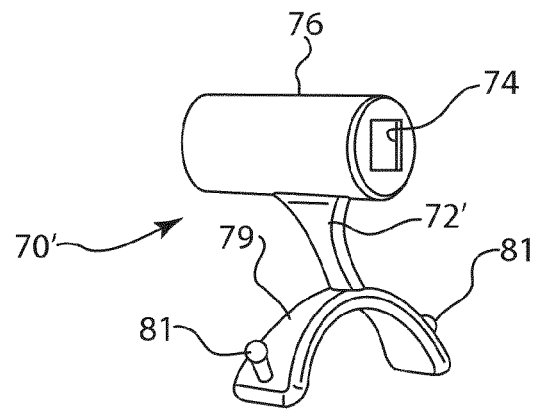
FIG. 9 is shows a perspective view of another embodiment of a tailpiece useful with a prosthesis system in accordance with the present invention.

Note that other forms of tailpiece can be used instead of the tailpiece 70 of FIGS. 7 and 8. For example, FIG. 9 shows a further embodiment of a tailpiece 70' that can be used in place of the tailpiece 70 in the jigs 40, 40' of FIGS. 7-8. The tailpiece 70' is similar to tailpiece 70 in that it includes a bore 74 for receiving a spacing bar 60 (FIGS. 7 and 8) and an extension piece 72' dimensioned as to maintain parallelism between axis A-A' and axis B-B'. However, instead of the brace 78 for accepting a K-wire 80 of FIGS. 7 and 8, the tailpiece 70' of FIG. 9 includes a brace 79 that has a curvature designed to rest on the distal forearm of a patient, over the patient's skin covering the ulnar styloid. Tailpiece 70' may include lugs 81 to engage a strap (not shown) that keeps the tailpiece firmly attached to the patient's wrist. As such, the tailpiece 70' of FIG. 9 preempts the drilling of a K-wire to into the fovea 12a of the ulna to locate a first point on axis of rotation A-A'.

Referring now to FIGS. 10-16, therein will be described one particular method for using a jig to assist in the placement of a prosthesis device. For purposes of example, the method of the invention will be described in connection with the removal and replacement of the radial head of an elbow joint. However, it will be understood that the same principles can be applied to the replacement of other bone portions in other joints of the body.

Figure 10:
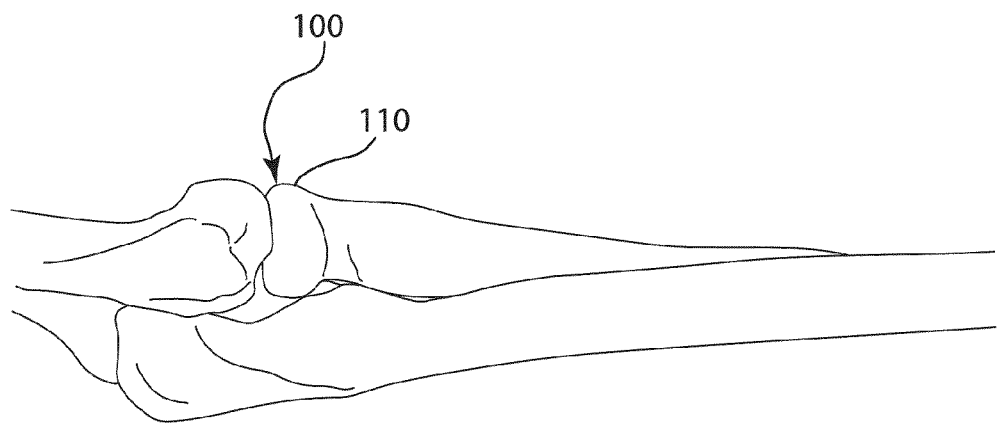
FIG. 10 is a partial view of a proximal radio-ulnar joint.
Figure 11:
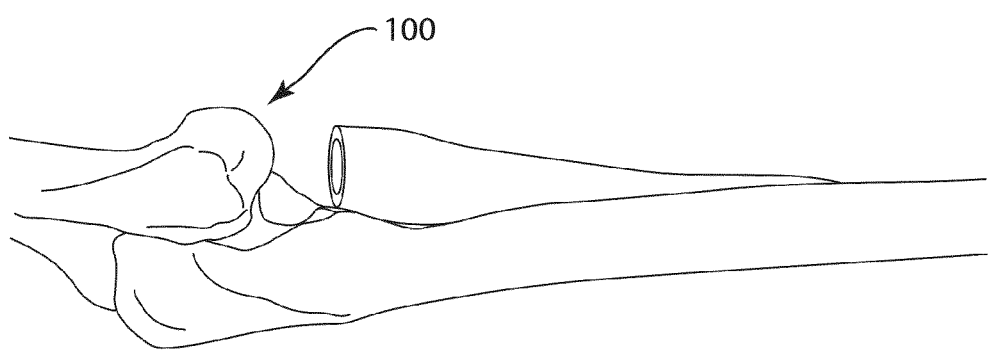
FIG. 11 is a partial view of the proximal radio-ulnar joint of FIG. 10 after the radial head has been removed.

An elbow joint 100 including a damaged radial head 110 to be removed and replaced is shown in FIG. 10. With the patient's forearm in pronation the surgeon makes a lateral incision to gain access to the joint 100 and removes the damaged radial head and/or radial head fragments. FIG. 11 shows the proximal radio-ulnar joint of FIG. 10, after the radial head has been removed. The radial head fragments are assembled and measured with or without the aid of a head sizing tray (not shown). The measured size is noted and used to select the closest sized prosthesis head 36, 36' of those provided.

A portion of the proximal end of the radius that remains exposed once the radial head has been removed is resected to expose the medullary canal. The radius is distracted laterally with the aid of forceps to gain access to the medullary canal. With a rasp (not shown), the medullary canal is expanded and the size of the rasp is noted, as this will match the diameter of the stem 31 of a radial head prosthesis 30 that will replace the native radial head. A properly sized planer (not shown) is used to smooth out the proximal radius at the face exposed by the resection in the previous step. FIG. 11 shows the elbow joint once the radius has been resected, rasped and planed.

Referring again to FIG. 11 the gap remaining between the now resected proximal end of the radius and the capitellum is measured with the aid of a neck sizing gauge (not shown). This size is recorded since it determines the length of the neck that will be required for the radial head prosthesis.

The surgeon now has the necessary measurements to select the appropriate parts of the radial head prosthesis 30 to be implanted in the patient which are: the diameter of the head 36; the diameter of the stem; and the length of the neck.

Figure 12:
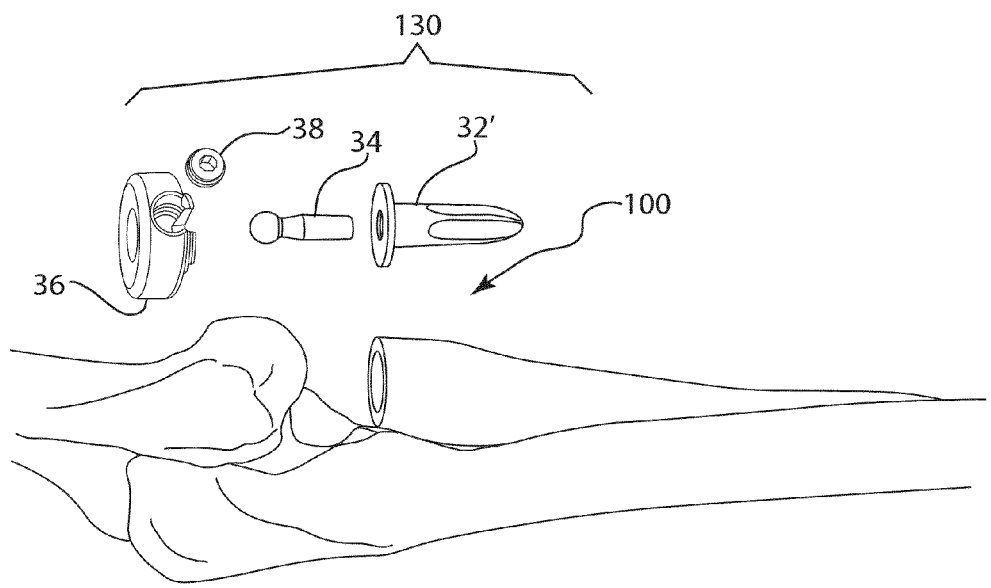
FIG. 12 is an exploded view of a prosthesis device of one embodiment of the present invention for replacement of the removed radial head.

If a unitary stem 31 (see FIG. 4C) is to be used, it is selected from those provided that most closely match the recorded measurement for diameter of the distal medullary anchor 32 and length of neck 34. Alternatively if a multipart stem (see FIGS. 4A and 4B) is to be used, it will be necessary to select individual distal medullary anchor portions 32 and necks 34 matching the corresponding measurements. The multipart anchor and neck are then mated or assembled as "unitary" stems prior to inserting in the medullary canal. FIG. 12 shows a radial head prostheses 130 to be assembled from a head 36, neck 34, distal medullary anchor portion 32' and set screw 38. It should be noted that all set screws 38, 38" can be pre-matched to the head 36 selected and provided as a set.

Figure 13:
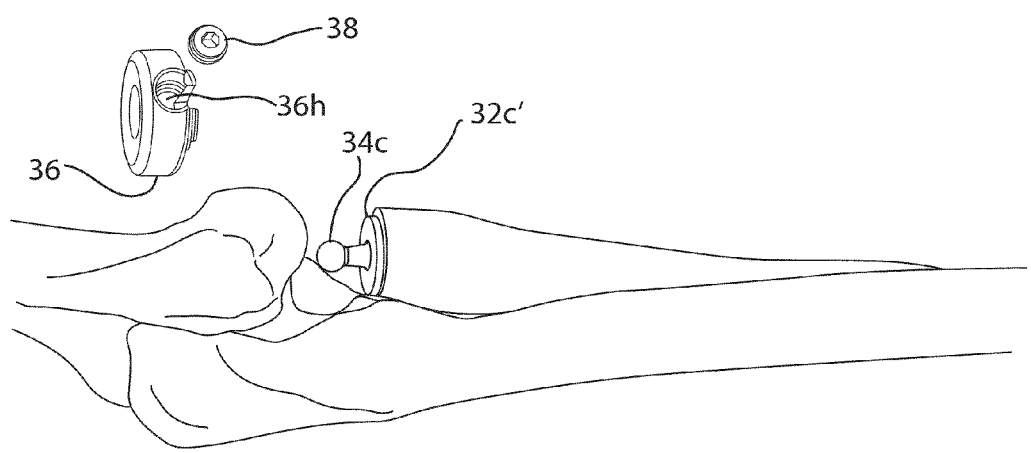
FIG. 13 is a partial view of the proximal radio-ulnar joint of FIG. 11 having the stem and neck of the prosthesis device of FIG. 12 inserted into the medullary canal of the radius.
Figure 14:
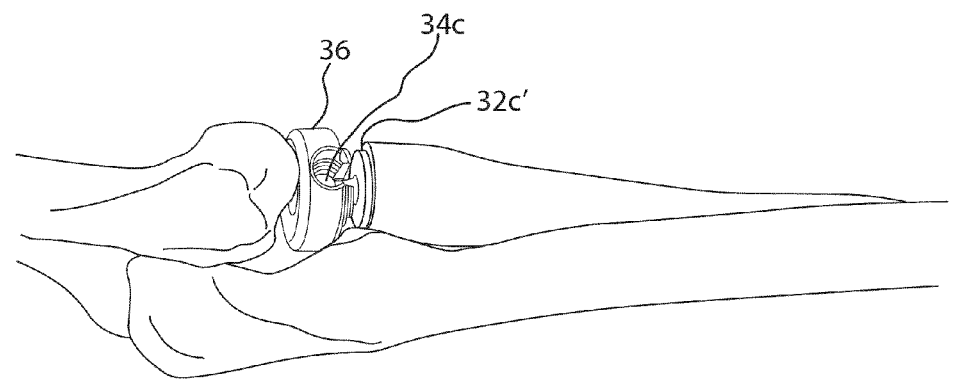
FIG. 14 is a partial view of a proximal radio-ulnar joint having the head, neck and shaft of a prosthesis device inserted in accordance with one particular embodiment of the present invention.
Figure 15A:
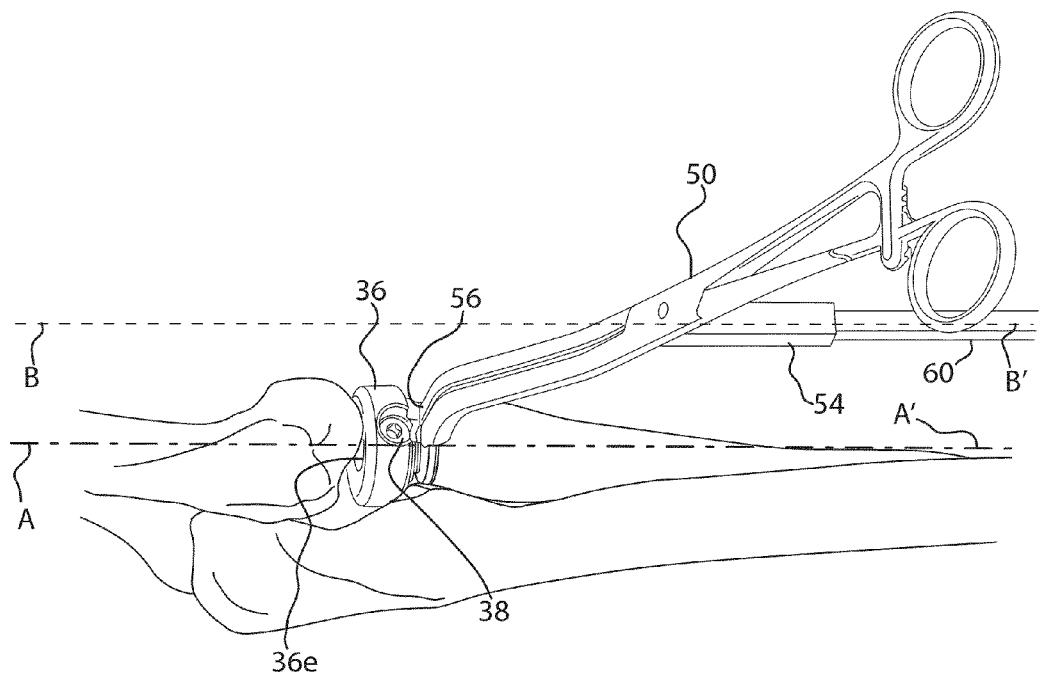
FIG. 15A shows the proximal radio-ulnar joint of FIG. 14 including a partial view of a jig for aligning the prosthesis head in the correct anatomical alignment relative to the capitellum, which alignment is fixed using a set screw, in accordance with one particular embodiment of the invention.
Figure 15B:
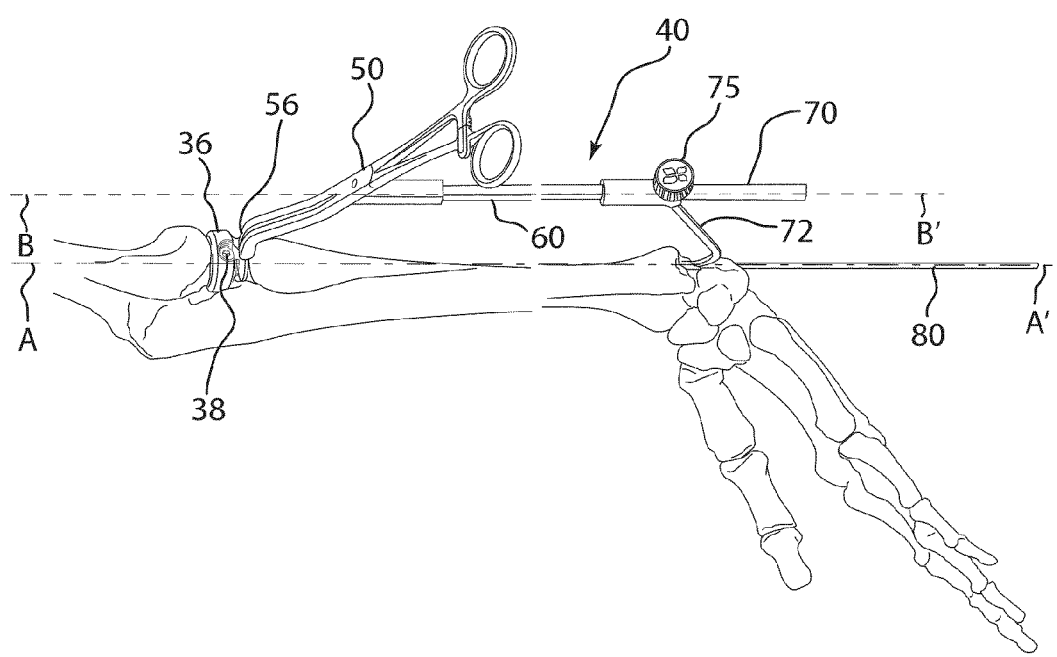
FIG. 15B shows the position of the jig of FIG. 15A relative to the axis of rotation of the forearm with the arm in pronation, i.e., with the palm of the hand facing downward, and a jig for aligning the head of a prosthesis in the correct anatomical alignment for the joint.
Figure 16:
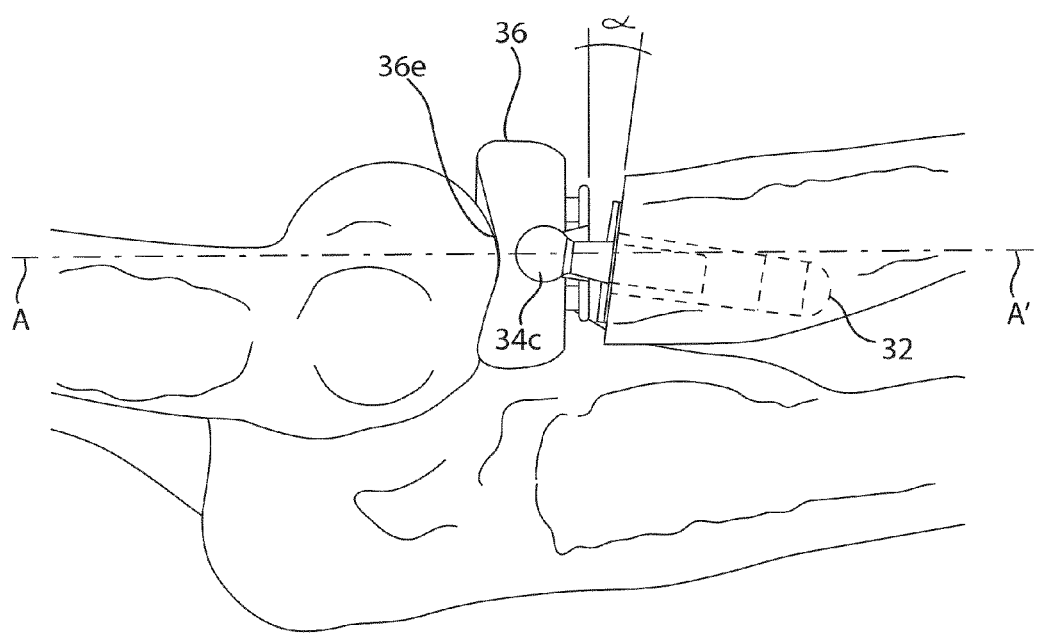
FIG. 16 is an enlarged view of the proximal radio-ulnar joint having a prosthesis device installed in accordance with the system and methods of one particular embodiment of the present invention.

The assembled stem 31 is then inserted into the radial medullary canal and tapped into place with an impactor (not shown) for a press fit. Note that, as shown in FIG. 13, after the medullary anchor portion has been inserted into the canal and press fitted to the planed face of the radius, the flange 32c' and the neck 34, where the most proximal part is the ball 34c, remain exposed. After insertion of the stem 32, the head 36 is side loaded onto the neck 34. The ball 34c and waist portion 34b slide through the channel 36f and cavity 36a until the ball 34a is at the terminus of the cavity 36a and cannot travel any further. In this configuration, the ball 34c is entrapped horizontally in the cavity by the narrowed shoulders of the channel but still allows swiveling of the head relative to the neck. After insertion, the head 36 is then rotated 180 degrees so that the opening 36h through the sidewall of the head faces the lateral side of the elbow, as shown in FIG. 14. This allows access to opening 36h to insert, and, subsequently, advance the set screw 38 along the thread 36b, in order to fix the ball 34c between the distal face of the set screw 38 and a portion of the surface or the cavity 36a.

If using the jig 40 of FIG. 7, at the distal end of the forearm in pronation and with the wrist flexed, a K-wire 80 is drilled percutaneously into the fovea of the ulna in the general direction of the radial head. As can be seen in FIG. 7, brace 78 of the tailpiece 70 is then inserted over the K-wire 80 to abut with the skin of the wrist covering the ulnar fovea. Once in the desired position, the free-end of the K-wire can be bent against the brace 78, to prevent the tailpiece from sliding off the K-wire. This anchors one end of jig 40 into one point of axis A-A'. The clamping portion 56 of the handle or clamp 50 is now used to hold the head 36 at a position perpendicular to the axis of rotation of the joint. More particularly, after the head 36 has been engaged between the neck 34 and the capitellum, the clamp 50 at the proximal end of the jig 40 is used to grasp the lug 36c on the underside of the head 36. See, for example, FIGS. 7 and 15A-15B. Because an axis B-B' through the jig 40 is held parallel to the axis of rotation A-A' of the forearm in this configuration, the clamping end 56 of the jig 40 is actually holding the bottom surface of the dish 36e in a plane that is normal to the axis A-A' (as well as the axis B-B'). The head 36 swivels on the ball 34c to achieve this configuration. As such, the jig 40 is holding the head 36 at the correct anatomical conical angle "α" in the relevant planes relative to the neck and the rest of the prosthesis. This correct alignment can be observed in FIG. 16.

Once the jig 40 has been set, and the clamping portion 56 of the jig 40 is holding the head 36 at the desired angle for the correct anatomical alignment relative to the neck 34 of the prosthesis 130 and the capitellum of the humerus, the set screw 38 is inserted and advanced on the thread 36b until the set screw contacts and applies a non-trivial force to the ball 34c. The engagement of the harder set screw 38 and splines 36g against the softer ball 34c locks the head 36 and ball 34c together at the desired correct anatomical alignment, with the head being fixed at the desired angle on the ball 34c. Again, see, for example, FIG. 16.

Resultantly, the dish 36e of the prosthesis head 36 is locked in place at the correct anatomical alignment desired for contact with the capitellum, that is, the head 36 has been fixed to the stem at a precise angle α such that a plane tangential to the bottom of the dish 36e is normal to the axis of rotation A-A' of the forearm, thus eliminating wobble.

Figure 17A:
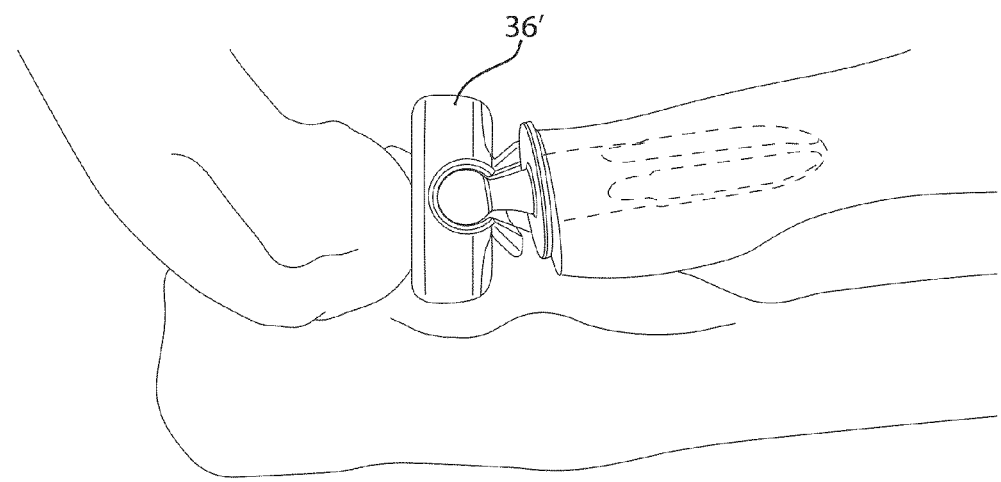
FIGS. 17A and 17B are enlarged views of the proximal radio-ulnar joint having a prosthesis device installed in accordance with the system and methods of another particular embodiment of the present invention
Figure 17B:
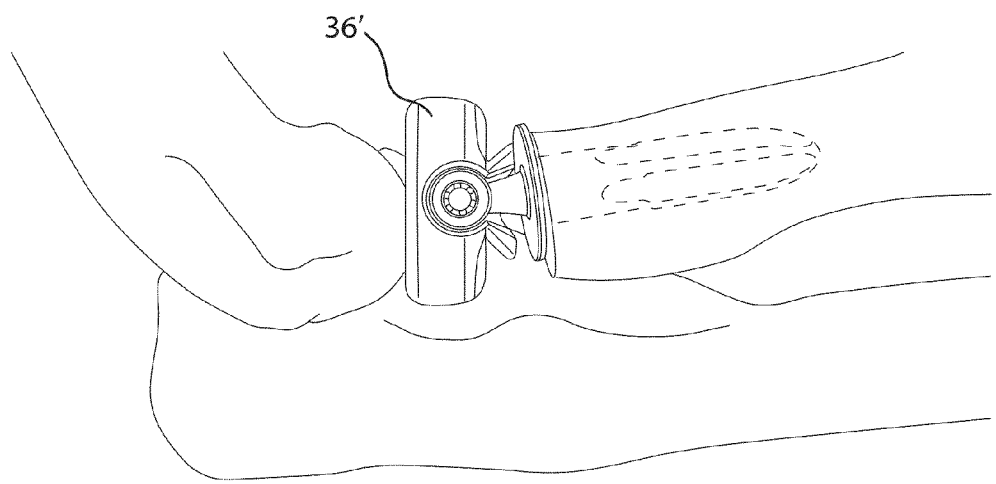

It is important to note that, although described in connection with the jig 40 (i.e., having the clamp 50 and tailpiece 70) of FIG. 7, for performing the alignment could be formed using the handle 50' and/or tailpiece 70', as described hereinabove. Similarly, although the prosthesis 130 was described as including the head 36, stem 32', neck 34 and set screw 38, it can be seen that another, head, stem, neck and/or set screw (including, but not limited to, head 36', stem 32, stem 32'', stem 32''', neck 34', and/or set screw 38') could be used in place of like components to form a prosthesis in accordance with the instant invention. For example, FIGS. 17A and 17B show the use of the head 36' in a prosthesis inserted by a method in accordance with the description given in connection with FIGS. 10-16, hereinabove, but using at least the handle 50' of FIG. 8 in place of the clamp 50 of FIG. 7.

Although the invention is illustrated and described herein in various embodiments, it is nevertheless not intended to be limited to only these details shown, since various modifications and structural changes may be made therein without departing from the spirit of the invention and within the scope and range of equivalents of the claims.

What is claimed is:

1. An alignable joint prosthesis system, comprising:
   a joint prosthesis, including:
      a head including an articular surface, an alignment portion and a chamber, the articular surface including a bottom;
      a stem including an anchor portion configured for anchoring in a bone and a neck portion configured to mate with said head;
      said neck portion including a spherical protuberance;
      said chamber being configured to receive said spherical protuberance;
      said chamber additionally being configured to permit free rotation of said head about said spherical protuberance when said spherical protuberance is received in said chamber;
      a set screw configured to impede further rotation of said spherical protuberance in said chamber; and
   a jig, including:
   a handle portion including a grasping portion configured to mate with said alignment portion of said head and hold said head at a particular orientation relative to said neck portion while said grasping portion is engaged with said alignment portion, a center of said grasping portion defining a point on a first longitudinal axis;
   a tailpiece portion including an extension and a brace, said brace defining a second point on said first longitudinal axis;
   a spacing bar defining a second longitudinal axis through a length of said spacing bar, said handle portion engageable to a first end of said spacing bar, said tailpiece portion engageable at a second end of said spacing bar and said extension of said tailpiece portion dimensioned to cause said first longitudinal axis to be parallel to said second longitudinal axis; and
   said grasping portion configured to align said alignment portion of said head into a position such that an imaginary plane tangential to the bottom of said articular surface of said head is held perpendicular to said first longitudinal axis while said grasping portion is engaged with said alignment portion.

2. The alignable joint prosthesis system of claim 1, wherein said spherical protuberance passes through said sidewall of said head to enter said chamber.

3. The alignable joint prosthesis system of claim 1, wherein said anchor portion and said neck portion are formed as a single piece.

4. The alignable joint prosthesis system of claim 1, wherein said anchor portion and said neck portion are formed as separate pieces and are mated together to form said stem.

5. The alignable joint prosthesis system of claim 1, wherein the stem is configured to be received in the medullary canal of a radius and the head is sized to replace a radial head.

6. The alignable joint prosthesis system of claim 1, wherein said chamber includes a plurality of splines for engaging said spherical protuberance when said spherical protuberance is disposed in said chamber.

7. The alignable joint prosthesis system of claim 6, wherein said set screw includes a face for engaging said spherical protuberance and maintaining said spherical protuberance against said splines when said set screw is advanced a predetermined distance through said sidewall.

8. The alignable joint prosthesis system of claim 7, wherein the face is pointed.

9. The alignable joint prosthesis system of claim 1, wherein said stem includes a flange at an upper portion of the anchor portion, a top surface of said flange being disposed in a plane perpendicular to an axis through the length of said stem.

10. The alignable joint prosthesis system of claim 1, wherein said set screw is sized to be received through a sidewall of said head, said sidewall including a threaded portion for receiving said set screw, said threaded portion permitting the set screw to be advanced through said sidewall to abut said spherical protuberance when said protuberance is received in said chamber.

11. The alignable joint prosthesis system of claim 1, wherein said grasping portion includes a clamping portion that includes lugs configured to mate with indentations in said alignment portion.

12. The alignable joint prosthesis system of claim 1, wherein said grasping portion includes two parallel prongs configured to engage with correspondingly shaped dovetail sidewalls of said alignment portion.

13. The alignable joint prosthesis system of claim 1, wherein said brace of said tailpiece portion is configured as a sleeve capable of receiving a K-wire, the axis of said sleeve being collinear with said first axis.

14. The alignable joint prosthesis system of claim 1, wherein said brace is configured to rest on the forearm of a patient, said second point on said first longitudinal axis being a center point of an arc defined by a curvature of said brace.

15. The alignable joint prosthesis system of claim 1, wherein said tailpiece portion is movable along and fixable to said spacing bar.

16. A method for placing a prosthesis device in a joint, comprising the steps of:
   providing access to the joint;
   providing an alignable joint prosthesis system according to claim 1;
   removing a portion of a first bone of the joint to expose the medullary canal of the first bone;
   inserting an anchoring portion of a stem into the exposed medullary canal of the first bone, the stem including a neck portion disposed at one end of the anchoring portion, the neck portion extending outside of the exposed medullary canal;

side-loading a head onto the neck, the head including a first surface configured to engage a portion of a second bone in the joint;

after the inserting step, rotating the head on the neck to achieve a desired angle of the first surface relative to an axis through the length of the stem; and after the rotating step, using a set screw to impede further rotation of the head on the neck.

17. The method of claim 16, further comprising the steps of:

locating the jig on the patient parallel to an axis of rotation of the joint;

with the handle portion, grasping the alignment portion of the head to hold the head at a desired angle relative to the neck while the grasping portion is engaged with said alignment portion; and using the jig to hold the head at the desired angle prior to and/or during the locking step.

18. The method of claim 17, further comprising the steps of:

pronating the forearm of the patient prior to the inserting step; and and locating the jig on the forearm of the patient parallel to the axis of rotation of the radial-ulnar joint.

19. The method of claim 17, further comprising the steps of:

drilling a K-wire into a third bone of the joint; and aligning the jig on the K-wire.

20. The method of claim 19, wherein the K-wire is drilled into the fovea of the ulna.

21. The method of claim 17, wherein the locking step includes advancing a set screw through a sidewall of the head to engage a portion of the neck contained in a cavity of the head and to impede further rotation of the head about the neck.

* * * * *